United States Patent [19]

Yasuda et al.

[11] Patent Number: 4,843,072

[45] Date of Patent: Jun. 27, 1989

[54] ANTIHYPERTENSIVE PYRIDAZINONE AMINOISOPROPANOL DERIVATIVES

[75] Inventors: Kikuo Yasuda, Yokohama; Kenyu Shibata, Inagi; Seijiro Honma, Yokohama; Toshimi Seki, Kawasaki; Kohichi Hasumi, Machida; Takeshi Masuda, Yokohama; Akihiro Izumi, Machida; Tsutomu Ishimori, Kawasaki; Kotaro Gotanda, Kawasaki; Masako Uno, Kawasaki, all of Japan

[73] Assignee: Teikoku Hormone Mfg. Co., Ltd., Tokyo, Japan

[21] Appl. No.: 93,033

[22] Filed: Sep. 4, 1987

[30] Foreign Application Priority Data

Sep. 8, 1986 [JP] Japan .................................. 61-209673

[51] Int. Cl.$^4$ ..................... C07D 237/04; A61L 31/50
[52] U.S. Cl. .................................. 514/247; 544/239
[58] Field of Search ......................... 544/239; 514/247

[56] References Cited

PUBLICATIONS

Hauel, Chem. Abs., 98, 198261u (1983).

Primary Examiner—Mark L. Berch
Attorney, Agent, or Firm—Wenderoth, Lind & Ponack

[57] ABSTRACT

A pyridazinone derivative represented by the following general formula

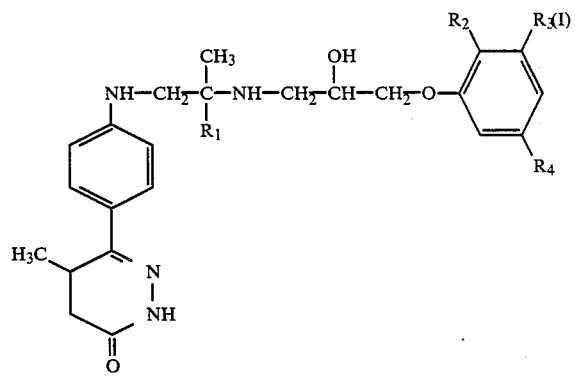

wherein $R_1$ represents a hydrogen atom or a methyl group, either one of $R_2$, $R_3$ and $R_4$ represents a hydrogen atom and the remaining two of them represent a lower alkyl group, a trifluoromethyl group, a halogen atom, a cyano group or a nitro group, and a salt thereof. The compounds are useful as antihypertensive agents.

7 Claims, No Drawings

ANTIHYPERTENSIVE PYRIDAZINONE AMINOISOPROPANOL DERIVATIVES

This invention relates to novel pyridazinone derivatives, and more specifically, to pyridazinone derivatives of the following formula

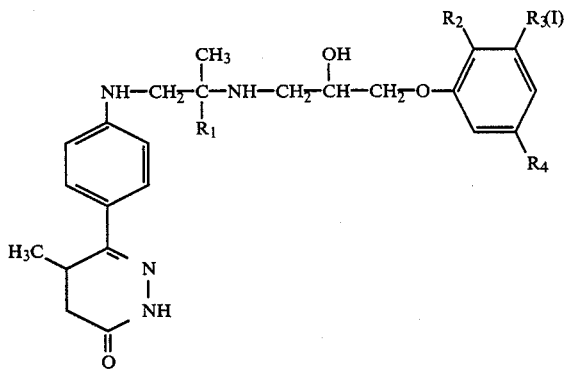

wherein $R_1$ represents a hydrogen atom or a methyl group, either one of $R_2$, $R_3$ and $R_4$ represents a hydrogen atom and the remaining two of them represent a lower alkyl group, a trifluoromethyl group, a halogen atom, a cyano group or a nitro group, and salts thereof, and to antihypertensive agents comprising the pyridazinone derivatives of formula (I) or salts thereof as active ingredients.

Many compounds having antihypertensive activity have previously been proposed. Vasodilators frequently used heretofore as antihypertensive agents generally have blood pressure lowering activity, but have the defect of inducing tachycardia. On the other hand, sympathetic nerve beta-receptor blocking (to be referred to as beta-blocking) agents are also used as antihypertensive agents. They have the advantage of not inducing tachycardia, but have the disadvantage that their antihypertensive action is slow and weak. Accordingly, in treating hypertensive patients, no sufficient effect can be expected by using a vasodilator and a beta-blocking agent singly. In the past clinical treatment, it has often been the practice to administer them together. This mode of administration, however, is troublesome to the patients, and not desirable for medication.

It has been desired therefore to develop an antihypertensive agent having the advantages of both the vasodilator-type antihypertensive agent and the beta-blocking antihypertensive agent. Recently, some publications were issued suggesting antihypertensive agents having both beta-blocking activity and vasodilating activity (see, for example, Japanese Laid-Open Patent Publications Nos. 13782/1976 and 32489/1979). These publications give little data substantiating the above two activities, or even when it was ascertained that the particular substance has both beta-blocking activity and vasodilating activity, these activities were very weak.

The present inventors previously proposed a certain class of hydrazinopyridazine derivatives and pyridazinone derivatives as antihypertensive agents having both excellent beta-blocking activity and vasodilating activity (see Japanese Laid-Open Patent Publications Nos. 142272/1981, 169675/1981 and 146570/1983).

Very recently, a dihydropyridazinone compound having a cyclopropylmethoxyethyl group was proposed (see Japanese Laid-Open Patent Publication No. 255776/1985).

These hydrazinopyrazine derivatives, pyridazinone derivatives and dihydropyridazinone compounds have both excellent beta-blocking activity and vasodilating activity, but still have the defect of inducing tachycardia.

The present inventors have made extensive investigations on an antihypertensive agent which does not induce tachycardia in spite of having both excellent beta-blocking activity and vasodilating activity. These investigations have led to the discovery that pyridazinone derivatives of formula (I) given above have both excellent beta-blocking activity and vasodilating activity as can be seen from pharmacological data given hereinbelow and yet do not induce tachycardia, and are suitable as antihypertensive agents.

In the present specification, the term "lower" means that a group or a compound qualified by this term has not more than 5, preferably not more than 3, carbon atoms.

The "lower alkyl group", as used in this invention, may be linear or branched. Examples are methyl, ethyl, n- or iso-propyl, and n-, iso-, sec- or tertbutyl. The methyl and ethyl groups are suitable.

The "halogen atom" represents fluorine, chlorine, bromine and iodine, and chlorine and bromine are suitable.

Among the compounds of formula (I) provided by this invention, (A) compounds of formula (I) in which $R_1$ is a methyl group and (B) compounds of formula (I) in which $R_2$ represents a methyl group, a chlorine atom or a cyano group and $R_3$ or $R_4$ represents a methyl group or a halogen atom are especially preferred from the standpoint of pharmacological effects.

Typical examples of the pyridazinone derivatives of formula (I) provided by this invention are shown immediately below and in Examples.

6-[4-[2-[3-(5-fluoro-2-nitrophenoxy)-2-hydroxypropylamino]-2-methylpropylamino]phenyl]-5-methyl-4,5-dihydro-3(2H)-pyridazinone, 6-[4-[2-[3-(2-methyl-5-nitrophenoxy)-2-hydroxypropylamino]-2-methylpropylamino]phenyl]-5-methyl-4,5-dihydro-3(2H)-pyridazinone, 6-[4-[2-[3-(2-ethyl-3-methylphenoxy)-2-hydroxypropylamino]propylamino]phenyl]-5-methyl-4,5-dihydro-3(2H)-pyridazinone, 6-[4-[2-[3-(3-chloro-5-methylphenoxy)-2-hydroxypropylamino]-2-methylpropylamino]phenyl]-5-methyl-4,5-dihydro-3(2H)-pyridazinone, 6-[4-[2-[3-(2-chloro-3-nitrophenoxy)-2-hydroxypropylamino]-2-methylpropylamino]phenyl]-5-methyl-4,5-dihydro-3(2H)-pyridazinone, 6-[4-[2-[3-(5-methyl-2-nitrophenoxy)-2-hydroxypropylamino]-2-methylpropylamino]phenyl]-5-methyl-4,5-dihydro-3(2H)-pyridazinone, 6-[4-[2-[3-(5-ethyl-2-methylphenoxy)-2-hydroxypropylamino]-2-methylpropylamino]phenyl]-5-methyl-4,5-dihydro-3(2H)-pyridazinone, 6-[4-[2-[3-(5-bromo-2-ethylphenoxy)-2-hydroxypropylamino]-2-methylpropylamino]phenyl]-5-methyl-4,5-dihydro-3(2H)-pyridazinone, 6-[4-[2-[3-(5-chloro-2-ethylphenoxy)-2-hydroxypropylamino]-2-methylpropylamino]phenyl]-5-methyl-4,5-dihydro-3(2H)-pyridazinone, 6-[4-[2-[3-(2-bromo-5-methylphenoxy)-2-hydroxy-propylamino]-2-methylpropylamino]phenyl]-5-methyl-4,5-dihydro-3(2H)-pyridazinone, 6-[4-[2-[3-(2-bromo-5-nitrophenoxy)-2-hydroxy-propylamino]-2-methylpropylamino]phenyl]-5-methyl-4,5-dihydro-3(2H)-pyridazinone, and 6-[4-[2-[3-(5-fluoro-2-methylphenoxy)-2-hydroxy-propylamino]-2-methylpropylamino]phenyl]-5-methyl-4,5-dihydro-3(2H)-pyridazinone.

According to this invention, there are also provided acid addition salts of the pyridazinone derivatives described above. Examples of the acid addition salts are salts with inorganic acids such as hydrochloric acid, hydrobromic acid, sulfuric acid, nitric acid and phosphoric acid, and salts with organic acids such as acetic acid, propionic acid, citric acid, lactic acid, and tartaric acid. Pharmaceutically acceptable acid addition salts are advantageously used.

According to this invention, the pyridazinone derivative of formula (I) may be produced by the reaction route shown by the following reaction scheme A.

Reaction Scheme A

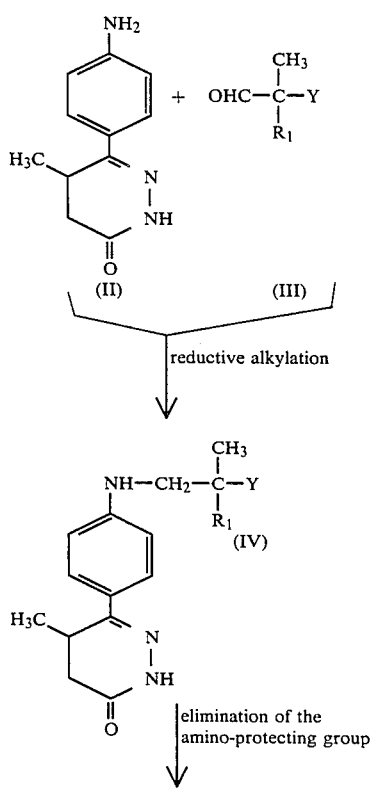

-continued
Reaction Scheme A

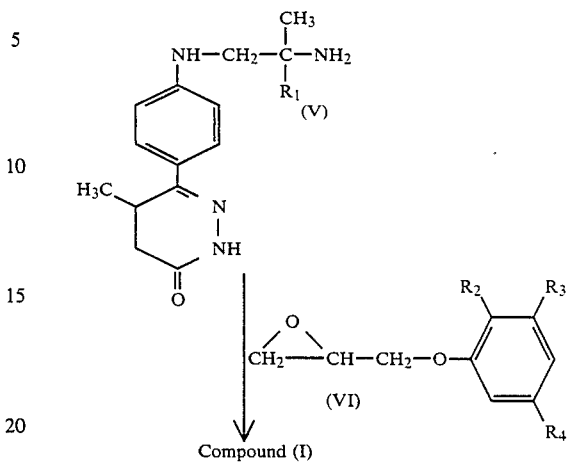

In the above formulae, Y represents a protected amino group, and $R_1$, $R_2$, $R_3$ and $R_4$ are as defined hereinabove.

The "protected amino group", as used herein, denotes an amino group (—$NH_2$) protected with a protective group which can be easily split off by ordinary amino-protecting group eliminating reactions such as hydrolysis, hydrazinolysis or hydrogenolysis. Examples of the amino-protecting group are phthaloyl, benzyloxycarbonyl, t-butoxycarbonyl and acetyl groups.

In the reaction scheme A, reductive alkylation of the compound of formula (II) with the aldehyde of formula (III) is carried out generally by contacting the compound of formula (II) with the aldehyde of formula (III) in an inert medium and reducing the resulting Schiff base. Example of the inert medium are aromatic hydrocarbons such as toluene, benzene and xylene, ethers such as dioxane, tetrahydrofuran, diethyl ether and dimethoxyethane, amides such as dimethylformamide, and alcohols such as methanol and ethanol.

Reduction of the Schiff base may be carried out (a) by causing the compound of formulae (II), the aldehyde of formula (III) and a reducing agent to be simultaneously present together in the above reaction system, or (b) by forming the Schiff base from the compound of formula (II) and the aldehyde of formula (III) and then reducing the Schiff base.

Examples of the reducing agent that can be used in the simultaneous method (a) include metal hydrogen complex compounds such as sodium cyanoborohydride, sodium borohydride and lithium aluminum hydride, and formic acid. The reducing agent may be used in an amount of 0.25 to 10 moles, preferably 0.5 to 2 moles, per mole of the compound of formula (II). Suitably, the simultaneous method is carried out usually at a temperature between about 0° C. and the refluxing temperature of the reaction mixture, preferably between 10° C. and about 100° C.

The Schiff base forming reaction in the consecutive method (b) above may be carried out at room temperature. Preferably, it is carried out under reflux while removing the water formed. The resulting Schiff base may be reduced with the same reducing agent as above. Alternatively, it may be reduced catalytically using a reducing catalyst such as palladium-active carbon, palladium black, platinum-active carbon, platinum oxide or Raney nickel.

In any of the methods (a) and (b), the suitable amount of the aldehyde of formula (III) is generally 1 to 10 moles, preferably 1 to 3 moles, per mole of the compound of formula (II).

The compound of formula (IV) is obtained by the above reductive alkylation reaction described above. This compound is then subjected to an amino-protecting group elimination reaction.

Deprotection may be carried out by various methods depending upon the type of the amino-protecting group. Examples are shown below.

(a) Elimination of the phthaloyl or acetyl group is carried out by hydrazinolysis involving reaction with hydrazine in a solvent such as alcohol or dioxane, or alkaline hydrolysis involving heating with sodium hydroxide or potassium hydroxide in alcohol.

(b) Elimination of the benzyloxycarbonyl group is carried out, for example, by hydrogenolysis involving reaction in a stream of hydrogen in alcohol in the presence of a catalyst such as palladium-active carbon.

(c) The t-butoxycarbonyl group may be eliminated by acid hydrolysis involving reaction with hydrogen chloride or trifluoroacetic acid in an organic solvent.

The above reaction yields the compound of formula (V) which is then reacted with the compound of formula (VI) to form the desired compound of formula (I). The reaction of the compound of formula (V) with the compound of formula (VI) may be carried out in the absence of a solvent. Generally, however, it is carried out in an inert medium, for example alcohols such as methanol, ethanol, propanol and butanol, aromatic hydrocarbons such as benzene, toluene and xylene, and halogenated hydrocarbons such as dichloromethane, chloroform and tetrachloroethane. The reaction temperature is not strictly limited. Generally, it is about 20° C. to the refluxing temperature of the reaction mixture, preferably 50° to 100° C. The proportion of the compound of formula (VI) relative to the compound of formula (V) is neither critical and can be varied broadly. Generally, the compound of formula (VI) is advantageously used in a proportion of 0.5 to 20 moles, preferably 1 to 5 moles, per mole of the compound of formula (V).

The compound of formula (V) may be produced also by the following reaction route shown by Reaction Scheme B.

Reaction Scheme B

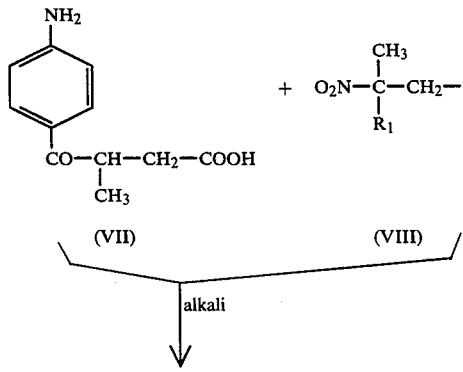

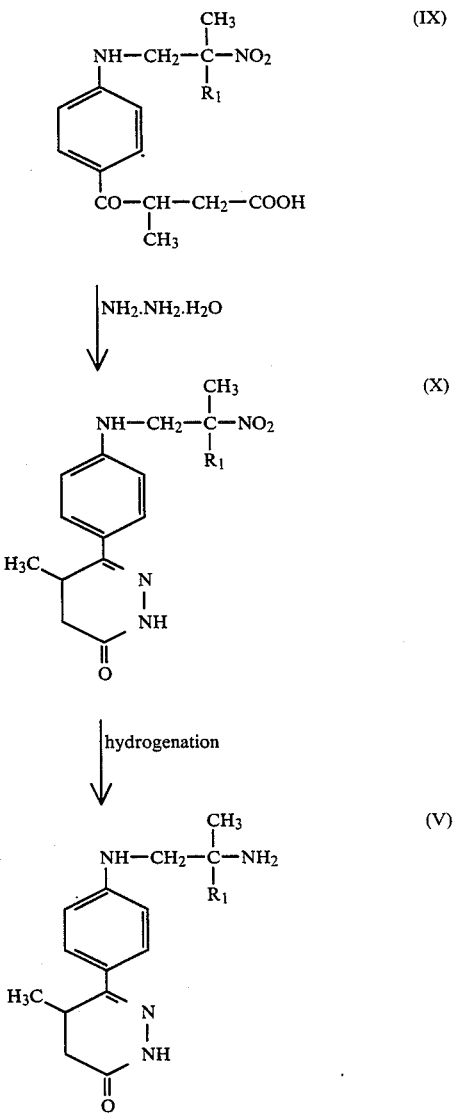

In the above formula, $R_1$ is as defined hereinabove.

In the reaction scheme B, the reaction of the compound of formula (VII) or its salt with the compound of formula (VIII) is carried out generally by condensation in a suitable inert reaction medium, for example, water, an alcohol such as methanol or ethanol, or a mixed solvent such as water-methanol or water-ethanol. This condensation is usually carried out under neutral to weakly alkaline conditions. To maintain the reaction system under such conditions, it is desirable to add sodium hydroxide, potassium hydroxide, sodium carbonate, potassium carbonate, sodium hydrogen carbonate, etc. to the reaction system. The condensation reaction proceeds in the absence of a catalyst, but generally it is preferred to carry it out in the presence of a reaction promoter such as benzyltriethyl ammonium chloride, benzyltrimethyl ammonium chloride or tetrabutyl ammonium bromide. The amount of the reaction promoter is not particularly restricted. Usually, its suitable amount is 0.01 to 0.02 mole per mole of the compound of formula (VII).

The compound of formula (VII) may be used in free form, but it is generally convenient, because of the ease of handling, to use it in the form of an acid addition salt such as a hydrochloride.

The amount of the compound of formula (VIII) relative to the compound of formula (VII) is not strictly limited and can be varied depending upon the reaction conditions, etc. Generally, the suitable amount of the compound of formula (VIII) is 1 to 5 moles, preferably 1 to 2 moles, per mole of the compound of formula (VII).

The reaction temperature in the condensation is about 60° C. to the refluxing temperature of the reaction mixture, preferably the refluxing temperature.

Thus, the compound of formula (IX) is formed. Since this product precipitates as crystals when an acid is added to the reaction mixture, it is separated by, for example, filtration, and reacted with hydrazine hydrate usually in an aqueous medium to cyclize it. This reaction is advantageously carried out at a temperature of about 60° to about 100° C., preferably 80° to 100° C. The amount of hydrazine hydrate is not particularly restricted. Generally, the suitable amount of hydrazine hydrate is 1 to 10 moles, preferably 2 to 5 moles, per mole of the compound of formula (IX).

The compound of formula (X) obtained by the above cyclization reaction is then hydrogenated to the desired compound of formula (V). Hydrogenation can be carried out by contacting the compound of formula (X) with hydrogen in a suitable inert medium, for example an alcohol such as methanol or ethanol, dimethylformamide or dimethylacetamide in the presence of a hydrogenation catalyst such as Raney nickel, palladium or palladiumcarbon. The suitable pressure of hydrogen used is generally 1 to 100 atmospheres, preferably 1 to 10 atmospheres, and the suitable reaction temperature is room temperature to 70° C.

The resulting compound of formula (V) can be converted to the compound of formula (I) by reacting it with the epoxy compound of formula (VI) by the method described hereinabove.

Thus, the desired compound of formula (I) can be obtained in good yields.

Recovery of the compound of formula (I) from the reaction mixture and its purification may be effected by methods known per se, for example extraction, column chromatography, thin-layer chromatography and recrystallization.

As required, the pyridazinone derivative of formula (I) produced as described above may be converted to salts by methods known per se, for example by treating it with an inorganic acid such as hydrochloric acid, hydrobromic acid, sulfuric acid, nitric acid or phosphoric acid, or an organic acid such as acetic acid, propionic acid, oxalic acid, maleic acid, citric acid, lactic acid, tartaric acid or methanesulfonic acid.

Generally, the pyridazinone derivatives of formula (I) provided by this invention are pharmacologically characterized by having both beta-blocking activity and vasodilating activity, and therapeutically excellent as long-lasting antihypertensive agents which do not induce tachycardia.

The following animal experiments will demonstrate that the compounds of formula (I) provided by this invention exhibit excellent beta-blocking activity and vasodilating activity (antihypertensive activity) without inducing tachycardia.

The compounds used in the animal experiments are represented by the following letters.

A: 6-[4-[2-[3-(2-chloro-5-methylphenoxy)-2-hydroxypropylamino]-2-methylpropylamino]phenyl]-5-methyl-4,5-dihydro-3(2H)-pyridazinone, B: 6-[4-[2-[3-(2,5-dichlorophenoxy)-2-hydroxypropylamino]-2-methylpropylamino]phenyl]-5-methyl-4,5-dihydro-3(2H)-pyridazinone, C: 6-[4-[2-[3-(2-cyano-5-chlorophenoxy)2-hydroxypropylamino]-2-methylpropylamino]phenyl]-5-methyl-4,5-dihydro-3(2H)-pyridazinone, D: 6-[4-[2-[3-(2-cyano-3-methylphenoxy)-2-hydroxypropylamino]-2-methylpropylamino]phenyl]-5-methyl-4,5-dihydro-3(2H)-pyridazinone, E: 6-[4-[2-[3-(2-nitro-3-methylphenoxy)-2-hydroxypropylamino]-2-methylpropylamino]phenyl]-5-methyl-4,5-dihydro-3(2H)-pyridazinone, F: 6-[4-[2-[3-(2-chloro-5-trifluoromethylphenoxy)-2-hydroxypropylamino]-2-methylpropylamino]-phenyl]-5-methyl-4,5-dihydro-3(2H)-pyridazinone.

The following compounds G and H were used as control compounds.

G: N-[4-(5-methyl-4,5-dihydro-3(2H)-pyridazinon-6-yl]phenyl]-2-[3-(2-methylphenoxy)-2-hydroxypropylamino]-propanamide (Japanese Laid-Open Patent Publication No. 146570/1983)

H: N-[4-(5-methyl-4,5-dihydro-3(2H)-pyridazinon-6-yl]phenyl]-2-[3-(2-chlorophenoxy)-2-hydroxypropylamino]-propanamide (ibid.)

Testing methods

Male Wistar rats (body weight 300 to 400 g) anesthetized with pentobarbital-Na (60 mg/kg i.p.) are used. The blood pressure is directly measured by connecting a cannula inserted in the femoral artery to a pressure transducer.

(1) Measurement of beta-blocking activity

Isoprenaline (0.1 μg/kg i.v.) is administered to rats (three per group), and immediately then, the increase in heart rate is measured and recorded. The measured heart rate at this time is designated as $H_1$. Then, a suspension of each test compound in 2% Tween 80-physiological saline aqueous solution is administered through the cannula inserted into the femoral vein of the rats. Three minutes later, isoprenaline (0.1 μg/kg i.v.) is again administered, and immediately then, the increase in heart rate is measured and recorded. The heart rate measured at this time is designated as $H_2$. The percent inhibition of the heart rate is calculated from these measured values in accordance with the following equation.

$$\text{Percent inhibition of the heart rate} (\%) = 100 - \frac{H_2}{H_1} \times 100$$

The dose of the test compound is cumulatively increased and the above operation is repeated. From the results, a dose-response curve is drawn. From this curve, the dose of the test compound at a heart rate inhibition of 50% is determined. This dose is compared with the dose of propranolol, and the results are shown in Tale 1.

(2) Measurement of vasodilating activity (antihypertensive acivity)

Each test compound (suspended in 2% Tween 80-physiological saline aqueous solution) is intravenously administered to rats (three per group) in a dose of 1 mg/kg, and the blood pressure is recorded periodically over 40 minutes. The maximum value of the lowered blood pressures during this period is determined. The results are also shown in Table 1.

(3) Measurement of the heart rate

The heart rate is calculated from the blood pressure pulse wave. The results are also shown in Table 1.

TABLE 1

| Compound | beta-Blocking activity (propranolol = 1) | Antihypertensive activity | Heart rate |
|---|---|---|---|
| A | 1/6 | + | → |
| B | 1/6 | ++ | → |
| C | ½ | +++ | → |
| D | 2/5 | +++ | → |
| E | ½ | ++ | → |
| F | 1/6 | ++ | → |
| G | 4/5–1 | +++ | ↑ |
| H | 1 | +++ | ↑ |

In the table, the antihypertensive activity is expressed as follows:

+: 15–24 mmHg
++: 25–34 mmHg
+++: 35< mmHg

The arrows showing the heart rate have the following meanings.

→: Almost no change occurs
↑: The heart rate increases by 50 to 100/min.

The compounds of formula (I) provided by this invention can be administered as antihypertensive agents having both beta-blocking activity and vasodilating activity to man and other warm-blooded animals. The route of administration may be oral or parenteral (e.g., intramuscular, intravenous, subcutaneous, intrarectal, or sublingual).

For use as a medicament, the compound (I) of this invention may be formulated into various forms suitable for oral or parenteral administration. For example, it may be formulated by using nontoxic adjuvants normally used in drugs of this type, such as vehicles, binders, lubricants, disintegrants, antiseptics, isotonizing agents, stabilizers, dispersants, antioxidants, coloring agents, flavoring agents and buffers.

According to uses, the compound of this invention may be formulated into solid preparations such as tablets, hard capsules, soft capsules, granules, powders, pellets, pills and trouches, semisolid preparations such as suppositories, and liquid preparations such as injecting preparations, emulsions, suspensions and syrups. Specific examples of the nontoxic adjuvants that can be used include starch, gelatin, glucose, lactose, fructose, maltose, magnesium carbonate, talc, magnesium stearate, methyl cellulose, carboxymethyl cellulose or its salt, gum arabic, polyethylene glycol, alkyl p-hydroxybenzoates, syrup, ethanol, propylene glycol, Vaseline, carbowax, glycerol, sodium chloride, sodium sulfite, sodium phosphate, and citric acid. The above medicaments may contain other therapeutically useful drugs.

The content of the compound of formula (I) in the medicament varies depending upon its dosage form. Generally, solid and semisolid preparations desirably contain the compound (I) in a concentration of 5 to 100% by weight, and liquid preparations desirably contain it in a concentration of 0.1 to 10% by weight.

The dose of the compound (I) of this invention may be varied widely depending upon the type of the subject to be treated (man and other warm-blooded animals), the severity of its conditions, the physician's judgement, etc. Generally, it is 0.02 to 30 mg/kg, preferably 0.05 to 10 mg/kg. It can be administered in doses larger than the upper limit or smaller than the lower limit depending upon the condition of the subject and the physician's judgement. The above dose may be administered once or in several portions per day.

The following examples illustrate the present invention further.

All temperatures in these examples are in °C. NMR measurement was made by using tetramethylsilane as an internal standard.

EXAMPLE 1

6-[4-(2-amino-2-methylpropylamino)phenyl]-5-methyl-4,5-dihydro-3(2H)-pyridazinone:

1-a. A mixture of 2-amino-2-methyl-1-propanol (53 g), di-t-butyl dicarbonate (65 g) and water (500 ml) was stirred at room temperature for 1 hour. The reaction mixture was extracted with chloroform, and the chloroform layer was dried over MgSO$_4$. The solvent was evaporated under reduced pressure. The residue was recrystallized from hexane to give 2-(t-butoxycarbonylamino)-2-methyl-1-propanol (44.4 g).

NMR (CDCl$_3$)δ: 1.25 (6H, singlet), 1.43 (9H, singlet), 3.20–5.50 (2H, multiplet), 3.56 (2H, singlet).

1-b. While a mixture of 2-(t-butoxycarbonylamino)-2-methyl-1-propanol (22.7 g) obtained in (1-a), triethylamine (36.4 g) and dry DMSO (360 ml) was stirred at room temperature, a solution of sulfur trioxide-pyridine complex (57.3 g) in dry DMSO (360 ml) was added. The mixture was further stirred for 30 minutes. The reaction solution was diluted with water (3600 ml) and extracted with ether. The ether layer was washed with 10% citric acid, water and then saturated NaHCO$_3$, and dried over MgSO$_4$. The solvent was evaporated under reduced pressure. The residue was recrystallized from hexane to obtain 2-(t-butoxycarbonylamino)-2-methylpropanal (17.2 g).

NMR (CDCl$_3$)δ: 1.32 (6H, singlet), 1.44 (9H, singlet), 5.00 (1H, broad singlet), 9.39 (1H, singlet).

1-c. While a mixture of 6-(4-aminophenyl)-5-methyl-4,5-dihydro-3(2H)-pyridazinone (2.03 g), 2-butoxy-carbonylamino)-2-methylpropanal (2.43 g) obtained in (1-b) above, acetic acid (0.3 g) and methanol (50 ml) was stirred at room temperature, a solution of sodium cyanoborohydride (0.33 g) in methanol (50 ml) was added dropwise. The mixture was further stirred for 2 hours. The solvent was evaporated under reduced pressure, and the residue was dissolved in chloroform. The chloroform layer was washed with a 5% aqueous solution of sodium carbonate, and dried over MgSO$_4$. The solvent was evaporated, and the residue was purified by silica gel column chromatography (Wakogel C-200, CHCl$_3$) to give 6-[4-(2-t-butoxycarbonylamino-2-methylpropylamino)phenyl]-5-methyl-4,5-dihydro-3(2H)-pyridazi none (3.58 g).

NMR (CDCl$_3$)δ: 1.22 (3H, doublet, J=7 Hz), 1.34 (6H, singlet), 1.42 (9H, singlet), 2.18–2.91 (2H, multiplet), 3.05–3.54 (1H, multiplet), 3.31 (2H, singlet), 4.58 (1H, broad singlet), 6.58 (2H, doublet, J=9 Hz), 7.52 (2H, doublet, J=9 Hz), 8.59 (1H, broad singlet).

IR $\gamma_{cm-1}^{KBr}$: 1680 (CO).

1-d. The 6-[4-(2-t-butoxycarbonylamino-2-methylpropylamino)phenyl]-5-methyl-4,5-dihydro-3(2H)-pyridazinone (3.74 g) obtained in (1-c) above was dissolved in ethyl acetate (10 ml), and 15% hydrogen chloride-ethyl acetate solution (40 ml) was added. The mixture was stirred for 2 hours, and the solvent was evaporated under reduced pressure. The residue was dissolved in water, made alkaline with sodium carbonate, and extracted with chloroform. The extract was dried over MgSO$_4$, and the solvent was evaporated to give 6-[4-(2-amino-2-methylpropylamino)phenyl]-5-methyl-4,5-dihydro-3(2H)-pyridazinone (2.06 g).

Melting point: 184.4°–185.2° C.

NMR (CD$_3$OD)δ: 1.15 (3H, doublet, J=7 Hz), 1.16 (6H, singlet), 2.10–2.94 (2H, multiplet), 3.06 (2H, singlet), 3.10–3.63 (1H, multiplet), 6.64 (2H, doublet, J=7 Hz), 7.53 (2H, doublet, J=9 Hz).

IR $\gamma_{cm}-1^{KBr}$: 1680 (CO)

| | Elemental analysis (for C$_{15}$H$_{22}$N$_4$O): | | |
|---|---|---|---|
| | C (%) | H (%) | N (%) |
| Found: | 65.71 | 8.18 | 20.31 |
| Calculated: | 65.66 | 8.08 | 20.42 |

EXAMPLE 2

6-[4-(2-amino-2-methylpropylamino)phenyl]-5-methyl-4,5-dihydro-3(2H)-pyridazinone:

2-a. By operating in the same way as in Example 1, (1-b), 2-(benzyloxycarbonylamino)-2-methylpropanal was obtained from 2-(benzyloxycarbonylamino)-2-methyl-1-propanol.

NMR (CDCl$_3$)δ: 1.36 (6H, singlet), 5.05 (2H, singlet), 5.30 (1H, broad singlet), 7.29 (5H, singlet), 9.37 (1H, singlet).

IR $\gamma_{cm}-1^{KBr}$: 3330 (NH), 1740, 1680 (CO).

2-b. By treating 6-(4-aminophenyl)-5-methyl-4,5-dihydro-3(2H)-pyridazinone and 2-(benzyloxycarbonylamino)-2-methylpropanal obtained in 2-a above in the same way as in Example 1, (1-c), 6-[4-(2-benzyloxycarbonylamino-2-methylpropylamino)phenyl]-5-methyl-4,5-dihydro-3(2H)-pyridazinone was obtained.

NMR (CDCl$_3$)δ: 1.20 (3H, doublet, J=7 Hz), 1.37 (6H, singlet), 1.50–1.90 (2H, broad singlet), 2.10–3.00 (2H, multiplet), 3.00–3.60 (1H, multiplet), 3.35 (2H, broad singlet), 5.02 (2H, singlet), 6.56 (2H, doublet, J-9 Hz), 7.28 (5H, singlet), 7.52 (2H, doublet, J=9 Hz), 8.47 (1H, broad singlet).

IR $\gamma_{cm}-1^{KBr}$: 1700, 1670 (CO)

2-c. A mixture of 6-[4-(2-benzyloxycarbonylamino-2-methylpropylamino)phenyl]-5-methyl-4,5-dihydro-3(2H)-pyridazinone (0.50 g), 10% palladium-carbon (0.50 g) and methanol (40 ml) was stirred in a stream of hydrogen for 3 hours. The catalyst was removed by filtration, and the filtrate was concentrated under reduced pressure to give 6-[4-(2-amino-2-methylpropylamino)phenyl]-5-methyl-4,5-dihydro-3(2H)-pyridazinone(0.30 g).

EXAMPLE 3

6-[4-(2-amino-2-methylpropylamino)phenyl]-5-methyl-4,5-dihydro-3(2H)-pyridazinone:

3-a. 2-Methyl-2-phthaliminopropanol (10.02 g) was dissolved in a mixed solution of dicyclohexylcarbodiimide (DCC: 28.09 g), pyridine (3.7 ml), dimethyl sulfoxide (50 ml) and benzene (100 ml), and trifluoroacetic acid (1.7 ml) was added. The mixture was stirred overnight at room temperature. Acetic acid (2.5 ml) and water (2.5 ml) were added to decompose the excess of DCC. The precipitated crystals were removed by filtration. Water was further added, and the benzene layer was separated, and dried over MgSO$_4$. The solvent was evaporated under reduced pressure. The resulting crystalline residue was purified by silica gel column chromatography (Wakogel C-200, CHCl$_3$) to give 2-methyl-2-phthaliminopropanal (7.64 g).

NMR (CDCl$_3$) δ: 1.68 (6H, singlet), 7.70–7.90 (4H, multiplet), 9.61 (1H, singlet).

IR $\gamma_{cm}-1^{KBr}$: 1765, 1735, 1710 (CO).

3-b. While a mixture of 6-(4-aminophenyl)-5-methyl-4,5-dihydro-3-(2H)-pyridazinone (12.71 g), 2-methyl-2-phthaliminopropanal (17.66 g) obtained in (3-a), acetic acid (5.6 ml) and dry methanol (300 ml) was stirred, a solution of sodium cyanoborohydride (2.07 g) in dry methanol (100 ml) was slowly added dropwise to the mixture. After stirring overnight, the precipitated crystals were collected by filtration to obtain 6-[4-(2-methyl-2-phthaliminopropylamino)phenyl]-5-methyl-4,5-dihydro-3(2H)-pyridazinone (17.63 g).

Melting point: 215.8°–217.4° C.

NMR (CDCl$_3$) δ: 1.18 (3H, doublet, J=7 Hz), 1.75 (6H, singlet), 2.05–2.85 (2H, multiplet), 3.07–3.42 (1H, multiplet), 3.72 (2H, singlet), 6.56 (2H, doublet, J=9 Hz), 7.48 (2H, doublet, J=9 Hz), 7.67 (4H, singlet), 8.51 (1H, broad singlet).

IR $\gamma_{cm}-1^{KBr}$: 1770, 1710, 1685 (CO).

| | Elemental analysis (for C$_{23}$H$_{24}$N$_4$O$_3$): | | |
|---|---|---|---|
| | C (%) | H (%) | N (%) |
| Found: | 68.26 | 5.76 | 13.68 |
| Calculated: | 68.30 | 5.98 | 13.85 |

3-c. The 6-[4-(2-methyl-2-phthaliminopropylamino)phenyl]-5-methyl-4,5-dihydro-3(2H)-pyridazinone (13 g) obtained in (3-b) above, hydrazine hydrate (52 ml) and ethanol (130 ml) was refluxed for 2 hours. After cooling, the reaction mixture was filtered, and the filtrate was concentrated under reduced pressure. The residue was dissolved in chloroform, washed with water and dried over MgSO$_4$. The solvent was evaporated under reduced pressure. The residue was recrystallized from isopropanol to give 6-[4-(2-amino-2-methylpropylamino)phenyl]-5-methyl-4,5-dihydro-3(2H)-pyridazinone (7.35 g).

EXAMPLE 4

6-[4-(2-amino-2-methylpropylamino)phenyl]-5-methyl-4,5-dihydro-3(2H)-pyridazinone:

4-a. A mixture of γ-(p-aminobenzoyl)butyric acid hydrochloride (349.5 g), 2-methyl-2-nitro-1-propanol (222 g), sodium hydroxide (114.8 g), benzyltriethyl ammonium chloride (6.35 g) and water (1.5 liters) was refluxed for 40 hours. Concentrated hydrochloric acid (170 ml) was added to the reaction mixture to acidify it. The precipitated crystals were collected by filtration to give γ-[4-(2-methyl-2-nitropropylamino)benzoyl]-butyric acid (364.46 g).

Melting point: 160°–161° C.

NMR (CDCl$_3$) δ: 1.23 (3H, doublet, J=7 Hz), 1.66 (6H, singlet), 2.46 (1H, double doublet, J=16 and 6 Hz), 2.94 (1H, double doublet, J=12 and 8 Hz), 3.40–5.05 (2H, multiplet), 3.60–3.95 (1H, multiplet), 3.70 (2H, singlet), 6.61 (2H, doublet, J=9 Hz), 7.84 (2H, doublet, J=9 Hz).

| | Elemental analysis (for C$_{15}$H$_{20}$N$_2$O$_5$): | | |
|---|---|---|---|
| | C (%) | H (%) | N (%) |
| Found: | 58.47 | 6.55 | 8.98 |

-continued

Elemental analysis (for $C_{15}H_{20}N_2O_5$):

| | C (%) | H (%) | N (%) |
|---|---|---|---|
| Calculated: | 58.43 | 6.54 | 9.09 |

4-b. A mixture of γ-[4-(2-methyl-2-nitropropylamino)benzoyl]butyric acid (630.95 g), hydrazine hydrate (298 ml) and water (900 ml) was heated over a steam bath for 2 hours with stirring. The crystals were collected by filtration, washed with water and recrystallized from methanol to give 6-[4-(2-methyl-2-nitropropylamino)phenyl]-5-methyl-4,5-dihydro-3(2H)-pyridazinone (549.76 g).
Melting point: 187°–189° C.
NMR (CDCl$_3$) δ: 1.22 (3H, doublet, J=7 Hz), 1.65 (6H, singlet), 2.25–2.85 (2H, multiplet), 3.10–3.45 (1H, multiplet), 3.65 (2H, doublet, J=7 Hz), 4.27 (1H, triplet, J=7 Hz), 6.63 (2H, doublet, J=9 Hz), 7.59 (2H, doublet, J=9 Hz), 8.64 (1H, broad singlet).
IR $\gamma_{cm}-1^{KBr}$: 3370, 3240 (NH), 1680 (CO), 1530 (NO$_2$).

Elemental analysis (for $C_{15}H_{20}N_4O_3$):

| | C (%) | H(%) | N (%) |
|---|---|---|---|
| Found: | 59.30 | 6.61 | 18.29 |
| Calculated: | 59.19 | 6.62 | 18.41 |

4-c. A mixture of 6-[4-(2-methyl-2-nitropropylamino)phenyl]-5-methyl-4,5-dihydro-3(2H)-pyridazinone (412.6 g), Raney nickel (100 ml) and dimethylformamide (1.5 liters) was hydrogenated under atmospheric pressure. After the absorption of hydrogen ceased, the catalyst was removed by filtration. The filtrate was concentrated under reduced pressure. The residue was recrystallized from methanol to give 6-[4-(2-amino-2-methylpropylamino)phenyl]-5-methyl-4,5-dihydro-3(2H)-pyridazinone (340.39 g).

EXAMPLE 5

6-[4-[2-[3-(2-cyano-5-chlorophenoxy)-2-hydroxypropylamino]-2-methylpropylamino]phenyl]-5-methyl-4,5-dihydro-3(2H)-pyridazinone:
(1) Synthesis of 1-(2-cyano-5-chlorophenoxy)-2,3-epoxypropane
2-Cyano-5-chlorophenol (3.0 g), epichlorohydrin (6.0 g) and anhydrous potassium carbonate (4.2 g) were heated with stirring in ethanol for 2 hours. The organic layer was concentrated under reduced pressure. The residue was purified by silica gel chromatography to give 3.1 g of 1-(2-cyano-5-chlorophenoxy)-2,3-epoxypropane.
IR $\gamma_{cm}-1^{KBr}$: 2228 (CN)
Melting point: 90°–92° C.
NMR (CDCl$_3$) δ (ppm): 2.75–3.00 (2H, multiplet), 3.25–3.50 (1H, multiplet), 4.10 (1H, double doublet, J=12.5 and 6.0 Hz), 4.36 (1H, double doublet, J=12.5 and 3.0 Hz), 6.80–7.10 (2H, multiplet), 7.45 (1H, doublet, J=8.8 Hz).
(2) 6-[4-(2-amino-2-methylpropylamino)phenyl]-5-methyl-4,5-dihydro-3(2H)-pyridazinone (3 g) and the 1-(2-cyano-5-chlorophenoxy)-2,3-epoxypropane (2.3 g) obtained in (1) above were stirred at 60° to 70° C. for 24 hours in t-butanol (100 ml). The solvent was evaporated under reduced pressure. The residue was separated by silica gel chromatography (chloroform:methanol=20:1) to give 6-[4-[2-[3-(2-cyano-5-chlorophenoxy)-2-hydroxypropylamino]-2-methylpropylamino]phenyl]-5-methyl-4,5-dihydro-3(2H)-pyridazinone (4.6 g).
NMR (CDCl$_3$) δ: 1.20 (6H, singlet), 1.20 (3H, doublet, J=7 Hz), 2.15–3.40 (7H, multiplet), 3.04 (2H, broad singlet), 4.08 (3H, broad singlet), 4.55 (1H, broad singlet), 6.56 (2H, doublet, J=9 Hz), 6.80–7.65 (5H, multiplet), 8.91 (1H, broad singlet).
IR $\gamma_{cm}-1^{KBr}$: 2220 (CN), 1670 (CO)
6-[4-[2-[3-(2-cyano-5-chlorophenoxy)-2-hydroxypropylamino]-2-methylpropylamino]phenyl]-5-methyl-4,5-dihydro-3(2H)-pyridazinone (2.25 g) was dissolved in ethanol, and an ethanol solution of maleic acid (0.54 g) was added. After standing at room temperature, the precipitated crystals were collected by filtration to give the corresponding maleate (2.27 g).
Maleate
Melting point: 193°–199° C.

Elemental analysis (for $C_{29}H_{34}ClN_5O_7$):

| | C (%) | H (%) | N (%) |
|---|---|---|---|
| Found: | 57.98 | 5.83 | 11.82 |
| Calculated: | 58.04 | 5.71 | 11.67 |

The following compounds were obtained in the same way as in (3) above using organic acids corresponding to the following organic acid salts instead of maleic acid.
(4) Monoethyl maleate salt
Melting point: 153°–158° C.

Elemental analysis (for $C_{31}H_{38}ClN_5O_7$):

| | C (%) | H (%) | N (%) |
|---|---|---|---|
| Found: | 59.29 | 6.34 | 11.33 |
| Calculated: | 59.28 | 6.10 | 11.15 |

(5) Acetylglycinate
Melting point: 151°–155° C.

Elemental analysis (for $C_{29}H_{37}ClN_6O_6$):

| | C (%) | H (%) | N (%) |
|---|---|---|---|
| Found: | 57.74 | 6.22 | 14.02 |
| Calculated: | 57.95 | 6.20 | 13.98 |

(6) Pyruvate
Melting point: 138°–142° C.
(7) Acetate
Melting point: 100°–104° C.
(8) Propionate
Melting point 105°–109° C.
(9) Glycolate
Melting point: 113°–117° C.
(10) Lactate
Melting point: 114°–118° C.
(11) Fumarate
Melting point: 187°–192° C.
(12) p-Toluenesulfonate
Melting point: 172°–176° C.
(13) Phosphate
Melting point: 133°–137° C.

EXAMPLE 6

(1) A mixture of 6-[4-(2-amino-2-methylpropylamino)phenyl]-5-methyl-4,5-dihydro-3(2H)- pyridazinone (3 g), 1-(2,5-dichlorophenoxy)-2,3-epoxypropane (2.4 g) and t-butanol (100 ml) was stirred at 65° to 70° C. for 24 hours. The solvent was evaporated under reduced pressure. The residue was purified by silica gel column chromatography (Wakogel C-200, 120 g). From the chloroform/methanol (=50/1) eluted portion, 6-[4-[2-[3-(2,5-dichlorophenoxy)-2-hydroxypropylamino]-2-methylpropylamino]phenyl]-5-methyl-4,5-dihydro-3(2H)-pyridazinone (4.77 g) was obtained.
NMR (CDCl$_3$) δ: 1.20 (6H, singlet), 1.20 (3H, doublet, J=7 Hz), 2.10-3.45 (7H, multiplet), 3.01 (2H, broad singlet), 4.00 (3H, broad singlet), 4.50 (1H, broad singlet), 6.52 (2H, doublet, J=9 Hz) 6.70-7.35 (3H, multiplet), 7.49 (2H, doublet, J=9 Hz), 9.00 (1H, broad singlet).
IR $\gamma_{cm}-1^{KBr}$: 1670 (CO)

(2) 6-[4-[2-[3-(2,5-dichlorophenoxy)-2-hydroxypropylamino]-2-methylpropylamino]phenyl]-5-methyl-4,5-dihydro-3(2H)-pyridazinone (4.77 g) was dissolved in ethanol, and an ethanol solution of maleic acid (1.122 g) was added. After standing at room temperature, the precipitated crystals were collected by filtration to give the corresponding maleate (5.52 g).
Melting point: 200°-202° C.

| Elemental analysis (for C$_{28}$H$_{34}$Cl$_2$N$_4$O$_7$): | | | |
|---|---|---|---|
| | C (%) | H (%) | N (%) |
| Found: | 55.13 | 5.62 | 9.20 |
| Calculated: | 55.17 | 5.62 | 9.19 |

In the same way as in Example 1, the following compounds were produced (Examples 7 to 24).

EXAMPLE 7

6-[4-[2-[3-(2,3-dichlorophenoxy)-2-hydroxypropylamino]-2-methylpropylamino]phenyl]-5-methyl-4,5-dihydro-3(2H)-pyridazinone:
NMR (CDCl$_3$) δ: 1.20 (3H, doublet, J=7 Hz), 1.21 (6H, singlet), 2.10-3.60 (8H, multiplet), 3.03 (2H, broad singlet), 4.05 (3H, broad singlet), 6.55 (2H, doublet, J=9 Hz), 6.70-7.20 (3H, multiplet), 7.51 (2H, doublet, J=9 Hz), 9.03 (1H, broad singlet).
IR $\gamma_{cm}-1^{KBr}$: 1670 (CO)
Maleate m.p. 167.5°-169.5° C.

| Elemental analysis (for C$_{28}$H$_{34}$Cl$_2$N$_4$O$_7$): | | | |
|---|---|---|---|
| | C (%) | H (%) | N (%) |
| Found: | 55.07 | 5.62 | 9.32 |
| Calculated: | 55.17 | 5.62 | 9.19 |

EXAMPLE 8

6-[4-[2-[3-(2,3-dimethylphenoxy)-2-hydroxypropylamino]-2-methylpropylamino]phenyl]-5-methyl-4,5-dihydro-3(2H)-pyridazinone:
NMR (CDCl$_3$) δ: 1.19 (6H, singlet), 1.19 (3H, doublet, J=7 Hz), 2.03-3.55 (9H, multiplet), 2.08 (3H, singlet), 2.21 (3H, singlet), 3.97 (3H, broad singlet), 4.55 (1H, broad singlet), 6.40-7.20 (3H, multiplet), 6.52 (2H, doublet, J=9 Hz), 7.50 (2H, doublet, J=9 Hz), 8.88 (1H, broad singlet).
IR $\gamma_{cm}-1^{KBr}$: 1670 (CO)
Maleate m.p. 170.0°-172.5° C.

| Elemental analysis (for C$_{30}$H$_{40}$N$_4$O$_7$): | | | |
|---|---|---|---|
| | C (%) | H (%) | N (%) |
| Found: | 63.49 | 7.12 | 9.79 |
| Calculated: | 63.36 | 7.09 | 9.85 |

EXAMPLE 9

6-[4-[2-[3-(2,5-dimethylphenoxy)-2-hydroxypropylamino]-2-methylpropylamino]phenyl]-5-methyl-4,5-dihydro-3(2H)-pyridazinone:
NMR (CDCl$_3$) δ: 1.20 (6H, singlet), 1.21 (3H, doublet, J=7 Hz), 2.00-3.50 (9H, multiplet), 2.13 (3H, singlet), 2.29 (3H, singlet), 3.99 (3H, broad singlet), 4.18-4.78 (1H, multiplet), 6.44-7.06 (3H, multiplet), 6.56 (2H, doublet, J=9 Hz), 7.51 (2H, doublet, J=9 Hz), 8.60 (1H, broad singlet).
IR $\gamma_{cm}-1^{KBr}$: 1670 (CO)
Maleate m.p. 182.0°-185.0° C.

| Elemental analysis (for C$_{30}$H$_{40}$N$_4$O$_7$): | | | |
|---|---|---|---|
| | C (%) | H (%) | N (%) |
| Found: | 63.33 | 7.09 | 9.75 |
| Calculated: | 63.36 | 7.09 | 9.35 |

EXAMPLE 10

6-[4-[2-[3-(3,5-dimethylphenoxy)-2-hydroxypropylamino]-2-methylpropylamino]phenyl]-5-methyl-4,5-dihydro-3(2H)-pyridazinone:
NMR (CDCl$_3$) δ: 1.18 (6H, singlet), 1.19 (3H, doublet, J=7 Hz), 2.00-3.50 (9H, multiplet), 2.24 (6H, singlet), 3.95 (3H, singlet), 4.30-4.75 (1H, multiplet), 6.30-6.71 (3H, multiplet), 6.55 (2H, doublet, J=9 Hz), 7.51 (2H, doublet, J=9 Hz), 8.64 (1H, broad singlet).
IR $\gamma_{cm}-1^{KBr}$: 1670 (CO)
Maleate m.p. 145.5°-149.0° C.

| Elemental analysis (for C$_{30}$H$_{40}$N$_4$O$_7$): | | | |
|---|---|---|---|
| | C (%) | H (%) | N (%) |
| Found: | 63.40 | 7.10 | 9.85 |
| Calculated: | 63.36 | 7.09 | 9.85 |

EXAMPLE 11

6-[4-[2-[3-(3-chloro-2-methylphenoxy)-2-hydroxypropylamino]-2-methylpropylamino]phenyl]-5-methyl-4,5-dihydro-3(2H)-pyridazinone:
NMR (CDCl$_3$) δ: 1.19 (3H, doublet, J=7 Hz), 1.20 (6H, singlet), 2.10-3.50 (7H, multiplet), 2.19 (3H, singlet), 3.01 (2H, broad singlet), 3.98 (3H, broad singlet), 4.60 (1H, broad singlet), 6.50-7.10 (3H, multiplet), 6.53 (2H, doublet, J=9 Hz), 7.49 (2H, doublet, J=9 Hz), 9.05 (1H, broad singlet).
IR $\gamma_{cm}-1^{KBr}$: 1670 (CO)
Maleate m.p. 171.0°-174.5° C.

| Elemental analysis (for C$_{29}$H$_{37}$ClN$_4$O$_7$): | | | |
|---|---|---|---|
| | C (%) | H (%) | N (%) |
| Found: | 58.91 | 6.44 | 9.63 |
| Calculated: | 59.12 | 6.33 | 9.51 |

EXAMPLE 12

6-[4-[2-[3-(3-(5-chloro-2-methylphenoxy)-2-hydroxypropylamino]-2-methylpropylamino]phenyl]-5-methyl-4,5-dihydro-3(2H)-pyridazinone:

NMR (CDCl$_3$) δ: 1.19 (3H, doublet, J=7 Hz), 1.20 (6H, singlet), 2.10–3.60 (7H, multiplet), 2.11 (3H, singlet), 3.04 (2H, broad singlet), 3.97 (3H, broad singlet), 4.55 (1H, broad singlet), 6.54 (2H, doublet, J=8 Hz), 6.70–7.10 (3H, multiplet), 7.51 (2H, doublet, J=8 Hz), 8.85 (1H, broad singlet).

IR $\gamma_{cm}-1^{KBr}$: 1670 (CO)

Maleate m.p. 196.5°–199.0° C.

| Elemental analysis (for C$_{29}$H$_{37}$ClN$_4$O$_7$): | | | |
|---|---|---|---|
| | C (%) | H (%) | N (%) |
| Found: | 58.99 | 6.46 | 9.57 |
| Calculated: | 59.12 | 6.33 | 9.51 |

EXAMPLE 13

6-[4[2-[3-(2-chloro-5-methylphenoxy)-2-hydroxypropylamino]-2-methylpropylamino]phenyl]-5-methyl-4,5-dihydro-3(2H)-pyridazinone:

NMR (CDCl$_3$) δ: 1.21 (3H, doublet, J=7 Hz), 1.21 (6H, singlet), 2.10–3.70 (8H, multiplet), 2.30 (3H, singlet), 3.04 (2H, broad singlet), 4.04 (3H, broad singlet), 6.56 (2H, doublet, J=9 Hz), 6.65–7.30 (3H, multiplet), 7.52 (2H, doublet, J=9 Hz), 8.85 (1H, broad singlet).

IR $\gamma_{cm}-1^{KBr}$: 1670 (CO)

Maleate m.p 166°–167° C.

| Elemental analysis (for C$_{29}$H$_{37}$ClN$_4$O$_7$): | | | |
|---|---|---|---|
| | C (%) | H (%) | N (%) |
| Found: | 59.03 | 6.36 | 9.58 |
| Calculated: | 59.13 | 6.33 | 9.51 |

EXAMPLE 14

6-[4-[2-[3-(2-chloro-3-methylphenoxy)-2-hydroxypropylamino]-2-methylpropylamino]phenyl]-5-methyl-4,5-dihydro-3(2H)-pyridazinone:

NMR (CDCl$_3$) δ: 1.19 (6H, singlet), 1.20 (3H, doublet, J=7 Hz), 2.10–3.45 (7H, multiplet), 2.31 (3H, singlet), 3.01 (2H, broad singlet), 4.01 (3H, broad singlet), 4.55 (1H, singlet), 6.52 (2H, doublet, J=9 Hz), 6.65–7.30 (3H, multiplet), 7.50 (2H, doublet, J=9 Hz), 9.01 (1H, broad singlet)

IR $\gamma_{cm}-1^{KBr}$: 1670 (CO)

Maleate m.p. 148.5°–151° C.

| Elemental analysis (for C$_{29}$H$_{37}$ClN$_4$O$_7$): | | | |
|---|---|---|---|
| | C (%) | H (%) | N (%) |
| Found: | 59.00 | 6.51 | 9.65 |
| Calculated: | 59.12 | 6.33 | 9.51 |

EXAMPLE 15

6-[4-[2-[3-(2-chloro-5-trifluoromethylphenoxy)-2-hydroxypropylamino]-2-methylpropylamino]phenyl]-5-methyl-4,5-dihydro-3(2H)-pyridazinone:

NMR (CDCl$_3$) δ: 1.19 (3H, doublet, J=7 Hz), 1.21 (6H, singlet), 2.10–3.45 (9H, multiplet), 4.09 (3H, broad singlet), 4.60 (1H, broad singlet), 6.59 (2H, doublet, J=9 Hz), 7.00–7.70 (5H, multiplet), 9.30 (1H, broad singlet).

IR $\gamma_{cm}-1^{KBr}$: 1670 (CO)

Maleate m.p. 202.5°–204.5° C.

| Elemental analysis (for C$_{29}$H$_{34}$ClF$_3$N$_4$O$_7$): | | | |
|---|---|---|---|
| | C (%) | H (%) | N (%) |
| Found: | 54.11 | 5.31 | 8.50 |
| Calculated: | 54.16 | 5.33 | 8.71 |

EXAMPLE 16

6-[4-[2-[3-(2-chloro-5-cyanophenoxy)-2-hydroxypropylamino]-2-methylpropylamino]phenyl]-5-methyl-4,5-dihydro-3(2H)-pyridazinone:

NMR (CDCl$_3$) δ: 1.20 (3H, doulbet, J=7 Hz), 1.22 (6H, singlet), 2.10–3.50 (9H, multiplet), 4.09 (3H, broad singlet), 6.60 (2H, doublet, J=9 Hz), 6.70 (1H, broad singlet), 7.05–7.75 (5H, multiplet), 8.80 (1H, broad singlet).

IR $\gamma_{cm}-1^{KBr}$: 2230 (CN), 1680 (CO)

Maleate m.p. 187.0°–188.5° C.

| Elemental analysis (for C$_{29}$H$_{34}$ClN$_5$O$_7$): | | | |
|---|---|---|---|
| | C (%) | H (%) | N (%) |
| Found: | 57.97 | 5.77 | 11.77 |
| Calculated: | 58.04 | 5.71 | 11.67 |

EXAMPLE 17

6-[4-[2-[3-(2-chloro-5-nitrophenoxy)-2-hydroxypropylamino]-2-methylpropylamino]phenyl]-5-methyl-4,5-dihydro-3(2H)-pyridazinone:

NMR (CDCl$_3$) δ: 1.20 (3H, doublet, J=7 Hz), 1.22 (6H, singlet), 2.10–3.60 (9H, multiplet), 4.12 (3H, broad singlet), 4.50 (1H, broad singlet), 6.57 (2H, doublet, J=9 Hz), 7.10–7.90 (5H, multiplet), 8.70 (1H, broad singlet).

IR $\gamma_{cm}-1^{KBr}$: 1675 (CO), 1530 (NO$_2$)

Maleate m.p. 194.5°–196.5° C.

| Elemental analysis (for C$_{28}$H$_{34}$ClN$_5$O$_9$): | | | |
|---|---|---|---|
| | C (%) | H (%) | N (%) |
| Found: | 54.15 | 5.47 | 11.24 |
| Calculated: | 54.23 | 5.52 | 11.29 |

EXAMPLE 18

6-[4-[2-[3-(3-chloro-2-cyanophenoxy)-2-hydroxypropylamino]-2-methylpropylamino]phenyl]-5-methyl-4,5-dihydro-3(2H)-pyridazinone:

NMR (CDCl$_3$) δ: 1.21 (3H, doublet, J=7 Hz), 1.21 (6H, singlet), 2.10–3.60 (7H, multiplet), 3.07 (2H, broad singlet), 4.11 (3H, broad singlet), 4.60 (1H, singlet), 6.58 (2H, doublet, J=9 Hz), 6.85 (1H, broad doublet, J=8 Hz), 7.02 (1H, broad doublet, J=8 Hz), 7.22 (1H, triplet, J=8 Hz), 7.54 (2H, doublet, J=9 Hz), 9.13 (1H, broad singlet).

IR $\gamma_{cm}-1^{KBr}$: 2225 (CN), 1670 (CO)

Maleate m.p. 173.0°–174.5° C.

| Elemental analysis (for C$_{29}$H$_{34}$ClN$_5$O$_7$): | | | |
|---|---|---|---|
| | C (%) | H (%) | N (%) |
| Found: | 58.03 | 5.84 | 11.92 |
| Calculated: | 58.04 | 5.71 | 11.67 |

EXAMPLE 19

6-[4-[2-[3-(2-cyano-3-methylphenoxy)-2-hydroxypropylamino]-2-methylpropylamino phenyl]-5-methyl-4,5-dihydro-3(2H)-pyridazinone:
NMR (CDCl₃) δ: 1.18 (3H, doublet, J=7 Hz), 1.20 (6H, singlet), 2.00°3.52 (9H, multiplet), 2.42 (3H, singlet), 4.05 (3H, broad singlet), 4.60 (1H, broad singlet), 6.52 (2H, doublet, J=9 Hz), 6.50–7.30 (3H, multiplet), 7.48 (2H, doublet, J=9 Hz), 9.00 (1H, broad singlet).
IR $\gamma_{cm}-1^{KBr}$: 2230 (CN), 1670 (CO)
Maleate m.p. 163.5°–167.0° C.

| Elemental analysis (for C₃₀H₃₇N₅O₇): | | | |
|---|---|---|---|
| | C (%) | H (%) | N (%) |
| Found: | 62.13 | 6.25 | 11.93 |
| Calculated: | 62.15 | 6.43 | 12.08 |

EXAMPLE 20

6[4-[2-[3-(2-cyano-5-methylphenoxy)-2-hydroxypropylamino]-2-methylpropylamino]phenyl]-5-methyl-4,5-dihydro-3(2H)-pyridazinone: NMR (CDCl₃) δ: 1.20 (3H, doublet, J=7 Hz), 1.21 (6H, singlet), 2.10–3.60 (7H, multiplet), 2.36 (3H, singlet), 3.05 (2H, broad singlet), 4.06 (3H, broad singlet), 4.60 (1H, broad singlet), 6.57 (2H, doublet, J=9 Hz), 6.60–7.50 (3H, multiplet), 7.50 (2H, doublet, J=9 Hz), 8.76 (1H, broad singlet).
IR $\gamma_{cm}-1^{KBr}$: 2220 (CN), 1670 (CO)
Maleate m.p. 198.0°–200.5° C.

| Elemental analysis (for C₃₀H₃₇N₅O₇): | | | |
|---|---|---|---|
| | C (%) | H (%) | N (%) |
| Found: | 62.19 | 6.37 | 11.88 |
| Calculated: | 62.15 | 6.43 | 12.08 |

EXAMPLE 21

6-[4-[2-[3-(2,5-dinitrophenoxy)-2-hydroxypropylamino]-2-methylpropylamino]phenyl]-5-methyl-4,5-dihydro-3(2H)-pyridazinone:
NMR (CDCl₃) δ: 1.18 (3H, doublet, J=7 Hz), 1.20 (6H, singlet), 2.10–3.60 (7H, multiplet), 3.04 (2H, broad singlet), 3.90–4.40 (4H, multiplet), 6.52 (2H, doublet, J=9 Hz), 7.46 (2H, doublet), J=9 Hz), 7.80–7.95 (3H, multiplet), 9.02 (1H, broad singlet).
IR $\gamma_{cm}-1^{KBr}$: 1670 (CO), 1550 (NO₂)
Maleate m.p. 171.5°–173.5° C.

| Elemental analysis (for C₂₈H₃₄N₆O₁₁): | | | |
|---|---|---|---|
| | C (%) | H (%) | N (%) |
| Found: | 53.42 | 5.18 | 13.10 |
| Calculated: | 53.32 | 5.43 | 13.32 |

EXAMPLE 22

6-[4-[2-[3-(chloro-2-nitrophenoxy)-2-hydroxypropylamino]-2-methylpropylamino]phenyl]-5-methyl-4,5-dihydro-3(2H)-pyridazinone:
NMR (CDCl₃) δ: 1.21 (3H, doublet, J=7 Hz), 1.21 (6H, singlet), 2.05–3.55 (9H, multiplet), 4.11 (3H, broad singlet), 4.50 (1H, broad singlet), 6.57 (2H, doublet, J=9 Hz), 6.85–7.95 (5H, multiplet), 8.80 (1H, broad singlet).
IR $\gamma_{cm}-1^{KBr}$: 1685 (CO), 1540 (NO₂)
Maleate m.p. 186.5°–190.5° C.

| Elemental analysis (for C₂₈H₃₄ClN₅O₉): | | | |
|---|---|---|---|
| | C (%) | H (%) | N (%) |
| Found: | 54.26 | 5.59 | 11.32 |
| Calculated: | 54.23 | 5.52 | 11.29 |

EXAMPLE 23

6-[4-[2-[3-(3-methyl-2-nitrophenoxy)-2-hydroxypropylamino]-2-methylpropylamine]phenyl]-5-methyl-4,5-dihydro-3(2H)-pyridazinone:
NMR (CDCl₃) δ: 1.18 (3H, doublet, J=7 Hz), 1.19 (6H, singlet), 2.13–3.55 (9H, multiplet), 2.27 (3H, singlet), 4.06 (3H, broad singlet), 4.68 (1H, broad singlet), 6.60 (2H, doublet, J=9 Hz), 6.70–7.50 (3H, multiplet), 7.56 (2H, doublet, J=9 Hz), 9.40 (1H, broad singlet).
IR $\gamma_{cm}-1^{KBr}$: 1670 (CO), 1535 (NO₂)
Maleate m.p. 135.5°–137.5° C.

| Elemental analysis (for C₂₉H₃₇N₅O₉): | | | |
|---|---|---|---|
| | C (%) | H (%) | N (%) |
| Found: | 58.06 | 6.05 | 11.72 |
| Calculated: | 58.08 | 6.21 | 11.68 |

EXAMPLE 24

6-[4-[2-[3-(2methyl-3-nitriphenoxy)-2-hydroxypropylamino]-2-methylpropylamino]phenyl]-5-methyl-4,5-dihydro-3(2H)-pyridazinone:
NMR (CDCl₃) δ: 1.20 (3H, doublet, J=7 Hz), 1.20 (6H, singlet), 2.00–3.50 (9H, multiplet), 2.28 (3H, singlet), 4.03 (3H, broad singlet), 4.50 (1H, multiplet), 6.54 (2H, doublet, J=9 Hz), 6.90–7.70 (5H, multiplet), 8.80 (1H, broad singlet).
IR $\gamma_{cm}-1^{KBr}$: 1660 (CO), 1540 (NO₂)
Maleate m.p. 124.5°–126.5° C.

| Elemental analysis (for C₂₉H₃₇N₅O₉): | | | |
|---|---|---|---|
| | C (%) | H (%) | N (%) |
| Found: | 57.95 | 6.15 | 11.67 |
| Calculated: | 58.08 | 6.21 | 11.68 |

EXAMPLE 25

6-[4-[2-[3-(2-chloro-5-methylphenoxy)-2-hydroxyproylamino]propylamino]phenyl]-5-methyl-4,5-dihydro-3(2H)-pyridazinone:

(1) The same operation as in Example 1, (1-c) was carried out by using 6-(4-aminophenyl)-5-methyl-4,5-dihydro-3(2H)-pyridazinone (2.03 g), 2-butoxycarbonylamino)propanal (2.09 g), acetic acid (0.6 g) and sodium cyanoborohydride (0.33 g), to obtain 6-[4-(2-t-butoxycarbonylaminopropylamino)phenyl]-5-methyl-4,5-dihydro-3(2H)-pyridazinone (2.89 g).

NMR (CDCl₃) δ: 1.14 (3H, doublet, J=6 Hz), 1.22 (3H, doublet, J=7 Hz), 2.13–5.00 (8H, multiplet), 6.56 (2H, doublet, J=9 Hz), 7.54 (2H, doublet, J=9 Hz), 8.64 (1H, broad doublet).

(2) By treating the 6-[-(2-butoxycarbonylaminopropylamino)phenyl]-5-methyl-4,5-dihydro-3(2H)-pyridazinone obtained in (1) above by the same operation as in Example 1, (1-d), 6-[4-(2-aminopropylamino)-phenyl]-5-methyl-4,5-dihydro-3(2H)-pyridazinone was obtained.

NMR (CDCl$_3$) δ: 1.14 (3H, doublet, J=6 Hz), 1.15 (3H, doublet, J=7 Hz), 2.08-2.95 (2H, multiplet), 2.95-3.53 (3H, multiplet), 6.60 (2H, doublet, J=9 Hz), 7.53 (2H, doublet, J=9 Hz).

IR $\gamma_{cm}-1^{KBr}$: 1665 (CO).

By treating the 6-[4-(2-aminopropylamino)phenyl]-5-methyl-4,5-dihydro-3 (2H)-pyridazinone obtained in (2) above and 1-(2-chloro-5-methylphenoxy)-2,3-epoxypropane by the same operation as in Example 5, (2), 6-[4-[2-[3-(2-chloro-5-methylphenoxy)-2-hydroxypropylamino]propylamino]phenyl]-5-methyl-4,5-dihydro-3 (2H)-pyridazinone was obtained.

NMR (CDCl$_3$) δ: 1.18 (3H, doublet, J=6 Hz), 1.19 (3H, doublet, J=7 Hz), 2.14-3.49 (10H, multiplet), 2.28 (3H, singlet), 4.02 (3H, broad singlet), 4.27-4.80 (1H, multiplet), 6.53 (2H, doublet, J=9 Hz), 6.55-7.30 (3H, multiplet), 7.50 (2H, doublet, J=9 Hz), 8.95 (1H, broad singlet).

IR $\gamma_{cm}-1^{KBr}$: 1670 (CO)

The following examples illustrate the production of drugs containing the compounds of the invention.

EXAMPLE A

Tablets:

Examples of formulation of tablets containing 5 mg or 20 mg of the active ingredient per tablet are as follows:

|  | mg/tablet |
|---|---|
| Formulation 1-a (5 mg tablet) | |
| 6-[4-[2-[3-(2-cyano-5-chlorophenoxy)-2-hydroxypropylamino]-2-methylpropylamino]phenyl]-5-methyl-4,5-dihydro-3(2H)—pyridazinone | 5 |
| Lactose | 137.2 |
| Starch | 44.8 |
| Caboxymethyl cellulose calcium | 10 |
| Talc | 2 |
| Magnesium stearate | 1 |
|  | 200.0 |
| Formulation 1-b mg tablets) | |
| 6-[4-[2-[3-(2-cyano-5-chlorophenoxy)-2-hydroxypropylamino]-2-methylpropylamino]phenyl]-5-methyl-4,5-dihydro-3(2H)—pyridazinone | 20 |
| Lactose | 122.2 |
| Starch | 44.8 |
| Carboxymethyl cellulose calcium | 10 |
| Talc | 2 |
| Magnesium stearate | 1 |
|  | 200.0 |

Specifically, the above tablets were prepared by the following procedure. Crystals of 6-[4-[2-[3-(2-cyano-5-chlorophenoxy)-2-hydroxypropylamino]-2-methyl-propylamino]phenyl]-5-methyl-4,5-dihydro-3(2H)-pyridazinone maleate were pulverized and well mixed with lactose and starch. A 10% starch paste was added to the mixed powder and mixed with stirring to prepare granules. The granules were dried, and then adjusted to a particle size of about 840 microns. The granules were mixed with talc and magnesium stearate and the mixture was tableted.

EXAMPLE B

| Injectable preparation:- | |
|---|---|
| 6-[4-[2-[3-(2-cyano-5-chlorophenoxy)-2-hydroxypropylamino-2-methylpropylamino)phenyl-5- | 5 mg |
| methyl-4,5-dihydro-3(2H)-pyridazinone | |
| Macrogol 4000 | 30 mg |
| Polysorbate 20 | 4 mg |
| Sodium chloride | 9 mg· |
| Distilled water for injection to make | 1 ml |

Specifically, aseptically produced 6-[4-[2-[3-(2-cyano-5-chlorophenoxy)-2-hydroxypropylamino]-2-methylpropylamino]phenyl]-5-methyl-4,5-dihydro-3(2H)-pyridazinone was suspended in a solvent containing the above formulated amounts of Macrogol 4000, polysorbate 20 and sodium chloride. The pH of the suspension was adjusted to about 7.0, and it was filled in an ampoule and sealed up.

What is claimed is :

1. A pyridazinone derivative represented by the following formula

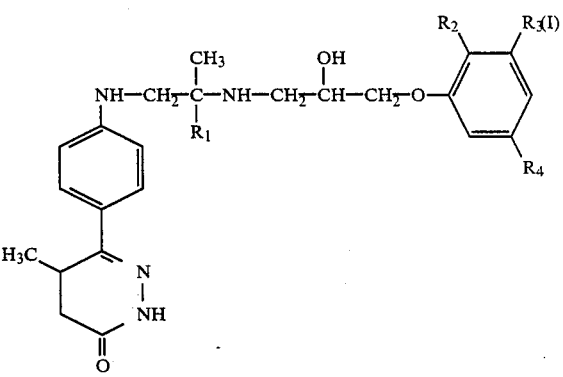

wherein R$_1$ represents a hydrogen atom or a methyl group, one of R$_2$, R$_3$ and R$_4$ represents a hydrogen atom and the remaining two of them represent a lower alkyl group, a trifluoromethyl group, a halogen atom, a cyano group or a nitro group, and a salt thereof.

2. The compound of claim 1 wherein R$_1$ represents a methyl group.

3. The compound of claim 1 wherein R$_2$ represents a methyl group, a chlorine atom or a cyano group, and R$_3$ or R$_4$ represents a methyl group or a halogen atom.

4. The compound of claim 1 which is 6-[4-]2-[3-(2-cyano-5-chlorophenoxy)-2-hydroxypropylamino]-2-methoxylpropylamino]phenyl]-5-methyl-4,5-dihydro-3(2H)-pyridazinone or 6-[4-[2-[3-(2,5-dichlorophenoxy)-2-hydroxypropylamino]-2-methylpropylamino]-phenyl]-5-methyl-4,5-dihydro-3(2H)-pyridazinone.

5. A pharmaceutical composition comprising an antihypertensively effective amount of the pyridazinone derivative of formula (I) or its pharmaceutically acceptable salt as set forth in claim 1 and pharmaceutically acceptable carrier or diluent.

6. A method of treating a patient with hypertension, which comprises administering an antihypertensive amount of the pyridazinone derivative of formula (I) or its pharmaceutically acceptable salt as set forth in claim 1 to the patient.

7. A compound represented by the following formula

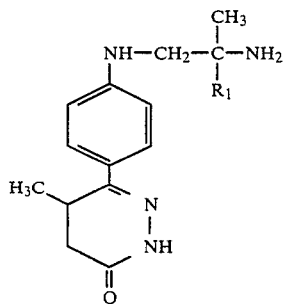
(V)
wherein $R_1$ represents a hydrogen atom or a methyl group.
* * * * *
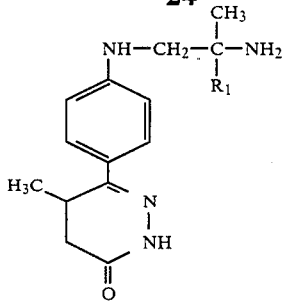
(V)
wherein $R_1$ represents a hydrogen atom or a methyl group.
* * * * *